(12) United States Patent
Waldron

(10) Patent No.: US 10,195,383 B2
(45) Date of Patent: *Feb. 5, 2019

(54) TRACHEOSTOMY TUBE WITH FILLETED FLANGE

(71) Applicant: Covidien LP, Mansfield, MA (US)

(72) Inventor: Paul Waldron, Galway (IE)

(73) Assignee: COVIDIEN LP, Mansfield, MA (US)

( * ) Notice: Subject to any disclaimer, the term of this patent is extended or adjusted under 35 U.S.C. 154(b) by 291 days.

This patent is subject to a terminal disclaimer.

(21) Appl. No.: 15/163,442

(22) Filed: May 24, 2016

(65) Prior Publication Data

US 2016/0263335 A1 Sep. 15, 2016

Related U.S. Application Data

(63) Continuation of application No. 13/963,623, filed on Aug. 9, 2013, now Pat. No. 9,364,629, which is a
(Continued)

(51) Int. Cl.
*A61M 16/04* (2006.01)
*A61M 16/08* (2006.01)
(Continued)

(52) U.S. Cl.
CPC .... *A61M 16/0465* (2013.01); *A61M 16/0434* (2013.01); *A61M 16/0438* (2014.02); *A61M 16/0488* (2013.01); *A61M 16/0497* (2013.01); *A61M 16/0816* (2013.01); *A61M 25/02* (2013.01); *A61M 16/044* (2013.01); *A61M 25/00* (2013.01); *A61M 2025/028* (2013.01); *A61M 2025/0213* (2013.01)

(58) Field of Classification Search
CPC .......... A61M 16/0465; A61M 16/0497; A61M 16/0816; A61M 25/02; A61M 2025/0206; A61M 2025/0213
See application file for complete search history.

(56) References Cited

U.S. PATENT DOCUMENTS 4,649,913 A 3/1987 Watson et al.
5,042,478 A 8/1991 Kopala et al.
(Continued)

FOREIGN PATENT DOCUMENTS

WO 2008145965 A1 12/2008

OTHER PUBLICATIONS

International Search Report and Written Opinion for PCT Application No. PCT/US2011/028118 dated Jul. 7, 2011, 11 pgs.
(Continued)

*Primary Examiner* — Kristen Matter
(74) *Attorney, Agent, or Firm* — Fletcher Yoder PC

(57) ABSTRACT

Various embodiments of a tracheostomy tube having neck flanges with filleted ends are provided. In certain embodiments, the neck flange may include a fillet extending from a bottom surface of the neck flange to a tip of the neck flange. In addition, the filleted end may also be tapered from a top surface of the neck flange to the tip of the neck flange. The neck flange may also include several curved edges, such as curved edges from the tip of the neck flange to side surfaces of the neck flange, and a curved bottom surface from side surface to side surface of the neck flange.

20 Claims, 3 Drawing Sheets

Related U.S. Application Data continuation of application No. 12/732,432, filed on Mar. 26, 2010, now Pat. No. 8,522,788.

(51) Int. Cl.
*A61M 25/02* (2006.01)
*A61M 25/00* (2006.01)

(56) References Cited

U.S. PATENT DOCUMENTS

| | | | |
|---|---|---|---|
| 5,305,742 A | 4/1994 | Styers et al. | |
| 6,071,255 A | 6/2000 | Salvatore | |
| 6,105,573 A | 8/2000 | Delaplane et al. | |
| 6,105,577 A | 8/2000 | Varner | |
| 6,772,758 B2 | 8/2004 | Lambert | |
| D543,279 S | 5/2007 | Numata | |
| 7,328,702 B2 | 2/2008 | Gostelow | |
| D576,276 S | 9/2008 | Osypka | |
| D578,640 S | 10/2008 | Ng et al. | |
| D581,045 S | 11/2008 | Sudo | |
| D593,679 S | 6/2009 | Bartlett et al. | |
| D607,100 S | 12/2009 | Uchida et al. | |
| D620,591 S | 7/2010 | Young | |
| 8,522,788 B2 * | 9/2013 | Waldron | A61M 16/0434 128/207.14 |
| 9,364,629 B2 * | 6/2016 | Waldron | A61M 16/0434 |
| 2004/0094160 A1 | 5/2004 | McDonald | |
| 2005/0005941 A1 | 1/2005 | Bischoff | |
| 2005/0010238 A1 | 1/2005 | Potter et al. | |
| 2005/0144761 A1 | 7/2005 | Hatcher | |
| 2005/0161047 A1 | 7/2005 | Briggs | |
| 2005/0188993 A1 | 9/2005 | Steeves et al. | |
| 2006/0041230 A1 | 2/2006 | Davis | |
| 2006/0060201 A1 | 3/2006 | Beagle et al. | |
| 2008/0072911 A1 | 3/2008 | Flagler et al. | |
| 2008/0142003 A1 | 6/2008 | Depel | |
| 2009/0025730 A1 | 1/2009 | Pinel | |
| 2009/0145439 A1 | 6/2009 | Peichel | |

OTHER PUBLICATIONS

Silicone Air Cuff Tracheostorny Tubes, Pediatric & Neonatal TT, Adjustable Neck Flange TT; Arcadia Medical; http://www.arcadiamedical.com/arcadia/main.asp?cid=4&pid=2, Date = pre-Mar. 26, 2010.
Silicone Cuffless Adult Tracheostomy Tubes; Arcadia Medical; http://www.arcadiamedical.com/arcadia/main.asp?cid=4&pid=2, Date= pre-Mar. 26, 2010.
Bivona Adult Mid-Range Aire-Cuf Adjustable Neck Flange Hyperflex; Smiths Medical; http://www.smiths-medical.com/catalog/endotracheal-tubes, Date = pre-Mar. 26, 2010.
Rusch Tracheofix; Teleflex Medical—Rusch;http://www.teleflexmedical.com/prod_rusch.php, Date = pre-Mar. 26, 2010.
Rusch Adjustable Flange Pediatric; Teleflex Medical—Rusch; http://www.teleflexmedical.com/prod_rusch.php, Date = pre-Mar. 26, 2010.
Rusch QuickTrach; Teleflex Medical—Rusch; http://www.teleflexmedical.com/prod_rusch.php, Date = pre-Mar. 26, 2010.
Rusch Trach Cap & Conn. Set; Teleflex Medical—Rusch; http://www.teleflexmecdical.com/prod_rusch.php, Date = pre-Mar. 26, 2010.
Rusch Trach Collar; Teleflex Medical—Rusch; http://www.teleflexrnedical.com/prod_rusch.php, Date = pre-Mar. 26, 2010.
Rusch PercuQuick Trach Set; Teleflex Medical—Rusch; http://www.teleflexmedical.com/prod_rusch.php, Date = pre-Mar. 26, 2010.
Vario; Tracoe Medica GmbH: http://www.tracoe.com/products.html, Date = pre-Mar. 26, 2010.

* cited by examiner

TRACHEOSTOMY TUBE WITH FILLETED FLANGE

CROSS REFERENCE TO RELATED APPLICATION

The present application claims priority to U.S. patent application Ser. No. 13/963,623, filed Aug. 9, 2013, which is a continuation of U.S. Pat. No. 8,522,788, filed Mar. 26, 2010, the teaching of which are incorporated herein by reference for all purposes.

BACKGROUND

The present disclosure, according to certain embodiments, relates to medical device tubes, e.g., tracheostomy tubes, used in medical applications, and more particularly, to tracheostomy tubes having flanges designed to fit on or near the neck of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A medical device tube may include an outer cannula (slender tube that may be inserted into a body cavity) attached to an outer cannula connector. In certain devices, the outer cannula connector and outer cannula are adapted for insertion of a disposable inner cannula. One example of a medical device tube is a tracheostomy tube. The tracheostomy tube may have a curved "L" shape and the outer cannula connector may be attached to a flange. The tracheostomy tube provides an artificial airway for access to the patient's airway for airway management. The tracheostomy tube is introduced into a tracheotomy incision (i.e., a stoma) in the patient's neck that provides access to the patient's trachea.

The inner cannula may be inserted into the outer cannula connector and outer cannula after the tracheostomy tube has been placed into the patient's trachea. The inner cannula typically includes a connector for quick removal of the inner cannula from the outer cannula. For example, the inner cannula connector may removably attach to the outer cannula connector, so that the inner cannula may be removed quickly if an obstruction (e.g., plug of mucus, sputum, etc.) is formed. For example, a snap connector may be used to attach the inner cannula to the outer cannula. A mechanical ventilator hose may be removably coupled to the inner cannula to assist the patient in breathing, or in instances where an inner cannula is not used, a ventilator hose may be removably coupled to the outer cannula connector.

In many designs, the tracheostomy tube may be secured to the patient's neck by the flange, which may be connected to a neck strap, thus securing the artificial airway for spontaneous or mechanical ventilation of the patient. After the tracheostomy tube is placed in the patient's stoma, the flange is placed against the patient's neck and the neck strap is threaded through tie holes at far ends of the flange. The flange extends on either side of the connector, in a generally wing-like arrangement, and is often made of flexible material (e.g., soft plastic or rubber), that allows it to conform somewhat to the neck. As such, the neck strap holds the flange in place against the patient's neck the entire time the device is in place for ventilation. However, in known designs, the neck strap tends to hold the far edges of the flange against the patient's neck, or alternatively the far edges of the flange tend to hold the strap against the patient's neck in the area under the far edge of the flange, causing friction and irritation of the patient's skin due to movement and contact of the far edges of the flange and the neck strap.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
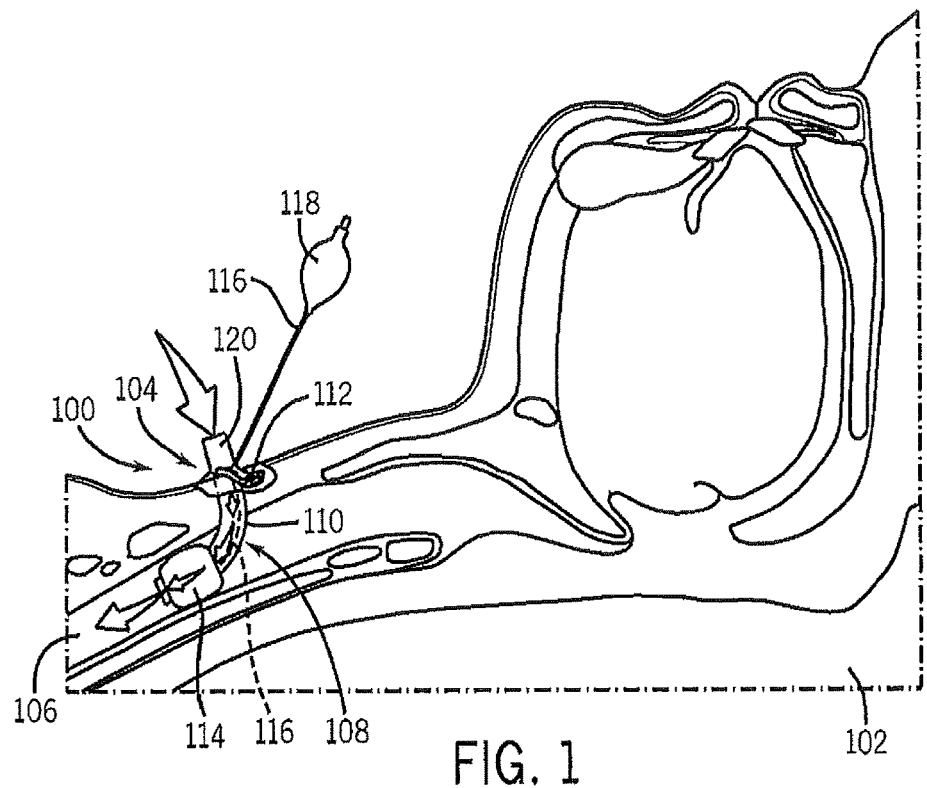
FIG. 1 is a schematic diagram of an exemplary tracheostomy tube, in accordance with aspects of the present invention.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As discussed in detail below, various embodiments of a tracheostomy tube having neck flanges with filleted ends are provided. Each filleted end may include a fillet from a point along the bottom surface of the neck flange to a tip of the neck flange. The neck flange includes tie holes. In certain embodiments, each tie hole may have an inner wall that abuts the bottom surface of the neck flange (e.g., at a point where the bottom surface meets the fillet end). However, in other embodiments, each tie hole may not have an inner wall that abuts the bottom surface. In other words, the cross section of the tie hole may be located entirely within the filleted end. In addition, the neck flange may include curved edges from side surfaces of the neck flange to the tip of the neck flange. Furthermore, the neck flange may include a curved bottom surface from side surface to side surface of the neck flange. The neck flange may also include a tapered surface from the top surface of the neck flange to the tip of the neck flange.

The devices and techniques provided herein may reduce the friction and irritation experienced by a patient due to movement of the neck flange and the tape and/or straps used to secure the neck flange against the patient's neck, or movement of the skin of the neck itself. For example, the filleted end of the neck flange may reduce the hard edges against the patient's skin, thereby reducing the friction and irritation experienced by the patient. In addition, the filleted nature of the end may enable the tape and/or straps to be elevated from the patient's skin, thereby reducing the contact of the tape and/or straps with the patient's skin. Furthermore, the curved edges of the filleted end and the bottom surface of the neck flange may further reduce the hard edges against the patient's skin, thereby further reducing the friction and irritation experienced by the patient, especially during extended use of the device. Although described herein as relating to tracheostomy tubes, the devices and techniques provided herein may actually be used for other types of medical device tubes having flanges that contact a patient's skin.

Turning now to the drawings, FIG. 1 is a schematic diagram of a tracheostomy tube 100, in accordance with aspects of the present invention. As illustrated, a patient 102 has a stoma 104 (opening) leading to his/her trachea 106. An outer cannula 108 of the tracheostomy tube 100 is inserted into the stoma 104 to provide an artificial airway for the patient 102. The outer cannula 108 may have a curved portion 110 (e.g., an L shape). A neck flange 112 of the tracheostomy tube 100 may be attached to the neck of the patient 102, for example, using tape and/or straps (not shown). When the neck flange 112 is attached to the neck of the patient 102, the tape and/or straps may cause ends of the neck flange 112 to cause friction and/or irritation of the skin of the patient 102. However, as described in greater detail below, the neck flange 112 is designed with filleted ends. The filleted ends reduce the amount of friction and irritation experienced by the patient 102 from attachment of the neck flange 112.

Optionally, an inflation cuff 114 may be located on the outer wall of the outer cannula 108, and an inflation lumen 116 may be located within the wall of the outer cannula 108. The inflation lumen 116 may be connected to the inflation cuff 114. An air valve port 118 may be used in combination with the inflation lumen 116 and the inflation cuff 114 such that the inflation cuff 114 may be inflated, creating an air and/or liquid sealing function between the outer cannula 108 and the trachea 106 air passage. The inflation cuff 114 may also position the outer cannula 108 within the trachea 106. In certain embodiments, more than one lumen may be provided in the wall of the outer cannula 108 and the additional lumens may be used for various other purposes. The inflation cuff 114 may be inflated with a fluid (typically air, although other fluids may include nitrogen, saline, water, and so forth). A connector 120 is configured to attach the tracheostomy tube 100 to various other tubes and conduits, such as an inner cannula (not shown) or a ventilator tube attached to a ventilator (not shown). In certain embodiments, the connector 120 may be a standard 15 mm connector.

Figure 2:
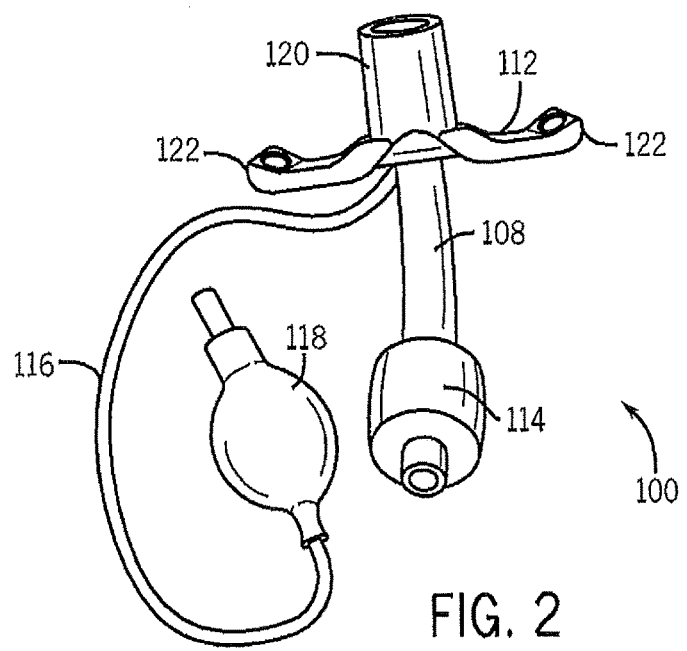
FIG. 2 is a perspective view of the tracheostomy tube of FIG. 1.

FIG. 2 is a perspective view of the tracheostomy tube 100. As illustrated, the connector 120 may be directly attached to the neck flange 112. As described above, the neck flange 112 has filleted ends 122 that may reduce the contact, and thus the amount of friction and irritation experienced by the patient 102 from movement and contact of the filleted ends 122 of the neck flange 112 and the tape and/or straps holding the neck flange 112 against the neck of the patient 102.

Figure 3:
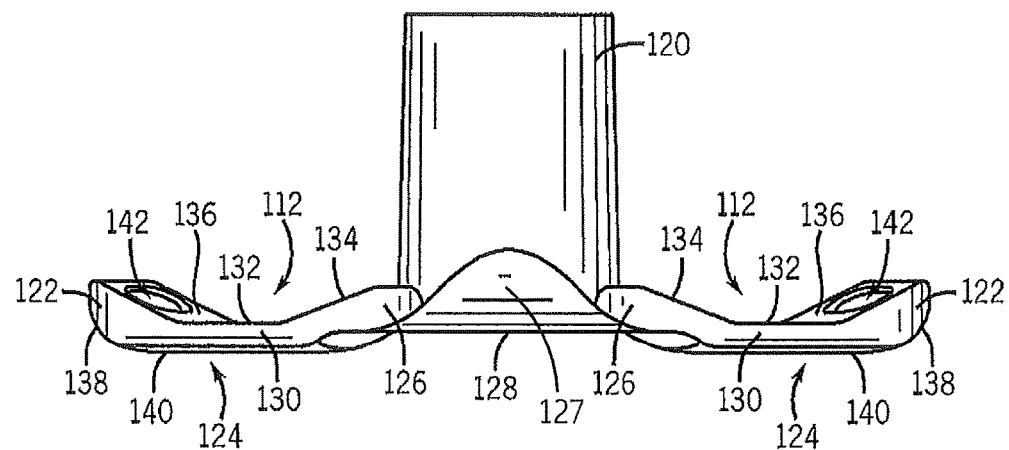
FIG. 3 is a perspective view of a neck flange and a connector of the tracheostomy tube of FIG. 1.

FIG. 3 is a perspective view of an exemplary neck flange 112 and the connector 120 of the tracheostomy tube 100. As illustrated, the neck flange 112 includes two flange sections 124 on opposite sides of the connector 120. Each flange section 124 is attached to the connector 120 via a connector end 126 of the flange section 124. For example, adjacent to a sloped surface 127 (e.g., angled surface) of the connector 120. The connector end 126 may extend from a distal end 128 of the connector 120 at an angle toward a main flange section 130. More specifically, in certain embodiments, the connector end 126 of each flange section 124 may extend toward a top surface 132 of the respective main flange section 130 via a tapered surface 134. In general, extending the connector end 126 toward the main flange section 130 at an angle away from the connector 120 minimizes the contact of the connector 120 with the patient's neck once the tracheostomy tube 100 is inserted in the stoma 104.

Similarly, in certain embodiments, the top surface 132 of each main flange section 130 may extend to the filleted end 122 via a tapered surface 136. Having a tapered surface 136 extending from the top surface 132 of the main flange section 130 may facilitate the filleting of the end 122. In other words, the fillet 138 extending from a bottom surface 140 of the main flange section 130 may otherwise reduce the cross-sectional area of the filleted end 122. However, having the tapered surface 136 extend from the top surface 132 of the main flange section 130 will increase the cross-sectional area of the filleted end 122, increasing the durability and resistance to bending of the filleted end 122. In addition, as described in greater detail below, the tapered surface 136 between the main flange section 130 and the filleted end 122 may facilitate a certain amount of isolation of the patient's neck from the tape and/or straps used to hold the tracheostomy tube 100 in place.

Figure 4:
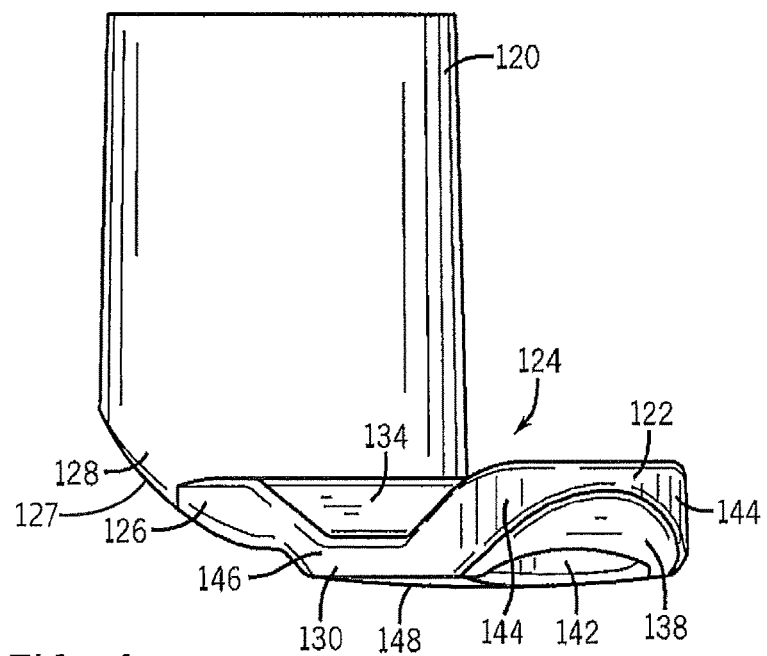
FIG. 4 is a perspective view of a flange section of the neck flange of FIG. 1.

FIG. 4 is a perspective view of an exemplary flange section 124 of the neck flange 112. As illustrated, each filleted end 122 includes a tie hole 142 through the filleted end 122. As described below, the tape and/or straps will be attached to the tracheostomy tube 100 using these tie holes 142. In general, the tie holes 142 are illustrated as being generally circular, but may also be other shapes. However, in certain embodiments, the circular nature of the tie holes 142 may be supplemented by curved edges of the filleted ends 142. In other words, each filleted end 122 may include curved edges 144 that extend from the filleted end 122 to side surfaces 146 of the respective main flange section 130. The curved edges 144 compliment the circular shape of the tie holes 142 such that the tape and/or straps used to hold the tracheostomy tube 100 in place may be allowed to move slightly relative to the filleted end 122, thereby providing a certain amount of flexibility to the attachment of the neck flange 112 against the patient's neck.

In addition, in certain embodiments, each main flange section 130 may include a curved bottom surface 148 extending from side surface 146 to side surface of the main flange section 130. As such, the curved nature of the bottom surface 148 may reduce the amount of friction and irritation of the patient's neck when the tracheostomy tube 100 is held in place. In other words, the curved nature of the bottom surface 148 may allow the main flange section 130 to roll slightly with respect to the patient's 102 skin, as opposed to contacting the patient's skin via hard edges. Indeed, the curved nature of the bottom surface 148 of the main flange section 130 may compliment the ability of the filleted end 122 of the neck flange 112 to isolate the patient's 102 skin from hard edges.

Figure 5:
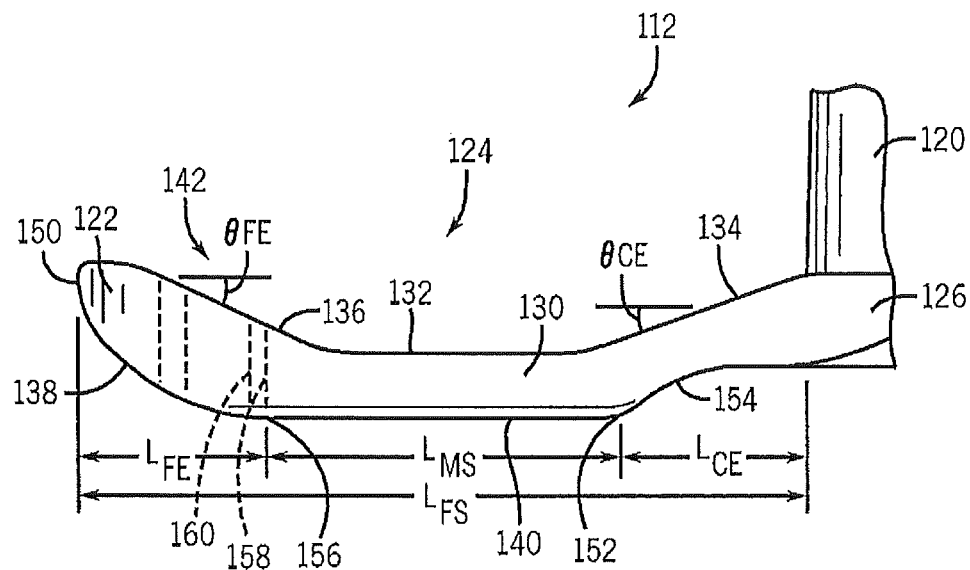
FIG. 5 is a side view of the flange section of the neck flange of FIG. 1, illustrating exemplary geometries of the flange and flange end.

FIG. 5 is a side view of an exemplary flange section 124 of the neck flange 112. Dimensions of the flange section 124 are illustrated to highlight features of the neck flange 112, in particular, the dimensions of the filleted end 122 of an exemplary flange section 124. As illustrated, the total length $L_{FS}$ of the flange section 124 may be approximately defined as the length $L_{FS}$ of the flange section 124 from the connector 120 to a tip 150 of the filleted end 122 of the flange section 124. Although specific dimensions may vary between tracheostomy tubes 100, the length $L_{FS}$ of the flange section 124 may be approximately 1.5-2.5 inches.

The length $L_{CE}$ of the connector end 126 may be defined as the length $L_{CE}$ of the connector end 126 from the connector 120 to approximately a point 152 on the bottom surface 140 of the main flange section 130 where the bottom surface 140 becomes relatively flat (e.g., generally the section of the flange section 124 that contacts the patient's neck when the tracheostomy tube 100 is in place). Here again, although specific dimensions may vary between tracheostomy tubes 100, the length $L_{CE}$ of the connector end 126 may be approximately 20-30% of the total length $L_{FS}$ of the flange section 124. In other words, the length $L_{CE}$ of the connector end 126 may be approximately 0.3-0.7 inches.

As described above, the connector end 126 may extend from the distal end 128 of the connector 120 at an angle toward the main flange section 130. More specifically, the connector end 126 may extend toward the top surface 132 of the main flange section 130 via the tapered surface 134. Although specific dimensions may vary between tracheostomy tubes 100, the angle $\theta_{CE}$ of the tapered surface 134 of the connector end 126 may be approximately 25-35 degrees. A bottom surface 154 of the connector end 126 may be curved (e.g., concave) and may generally have the same angle as $\theta_{CE}$ away from the connector 120.

In general, the main flange section 130 may be relatively flat. The length $L_{MS}$ of the main flange section 130 may be defined as the length $L_{MS}$ of the main flange section 130 from approximately the point 152 where the bottom surface 140 of the main flange section 130 meets the bottom surface 154 of the connector end 126 to approximately a point 156 where the bottom surface 140 of the main flange section 130 meets the fillet 138 of the filleted end 122. Although specific dimensions may vary between tracheostomy tubes 100, the length $L_{MS}$ of the main flange section 130 may be approximately 40-60% of the total length $L_{FS}$ of the flange section 124. In other words, the length $L_{MS}$ of the main flange section 130 may be approximately 0.6-1.4 inches.

The length $L_{FE}$ of the filleted end 122 may be defined as the length $L_{FE}$ of the filleted end 122 from approximately the point 156 where the bottom surface 140 of the main flange section 130 meets the fillet 138 of the filleted end 122 to the tip 150 of the filleted end 122. Although specific dimensions may vary between tracheostomy tubes 100, the length $L_{FE}$ of the filleted end 122 may be approximately 20-30% of the total length $L_{FS}$ of the flange section 124. In other words, the length $L_{FE}$ of the filleted end 122 may be approximately 0.3-0.7 inches.

As described above, the filleted end 122 may include a tapered surface 136 extending from the top surface 132 of the main flange section 130 to the tip 150 of the filleted end 122. Although specific dimensions may vary between tracheostomy tubes 100, the angle $\theta_{FE}$ of the tapered surface 136 of the filleted end 122 may be approximately 30-40 degrees. The fillet 138 of the filleted end 122 may generally have the same angle from the point 156 where the bottom surface 140 of the main flange section 130 meets the fillet 138 of the filleted end 122 to the tip 150 of the filleted end 122. However, the angle of the fillet 138 may generally be smaller near the point 156 where the bottom surface 140 of the main flange section 130 meets the fillet 138 of the filleted end 122 than near the tip 150 of the filleted end 122.

As also mentioned above, the filleted end 122 includes a tie hole 142 through the filleted end 122 through which the tape and/or straps are used to secure the tracheostomy tube 100 to the patient's neck. The tie holes 142 may be circular having an inner wall 158 that generally aligns with the point 156 where the bottom surface 140 of the main flange section 130 meets the fillet 138 of the filleted end 122. In other words, the tie holes 142 may have an inner wall 158 that abuts the bottom surface 140 of the main flange section 130. However, in certain embodiments, the tie holes 142 may have an inner wall 160 that is entirely on the filleted end 122 of the flange section 124. In other words, the tie holes 142 may not have an inner wall 160 that abuts the bottom surface 140 of the main flange section 130. As such, each tie hole 142 may either be located on a near end of the fillet 138 or at some point within the fillet 138 (e.g., with part of the fillet 138 on either side of the tie hole 142 along the length $L_{FS}$ of the flange section 124).

It should be understood that the above dimensions and angles are representative only, and that such dimensions and angles may be modified as appropriate to suit the particular device and intended patient demographic (e.g., pediatric, over-weight, male, etc.).

Figure 6:
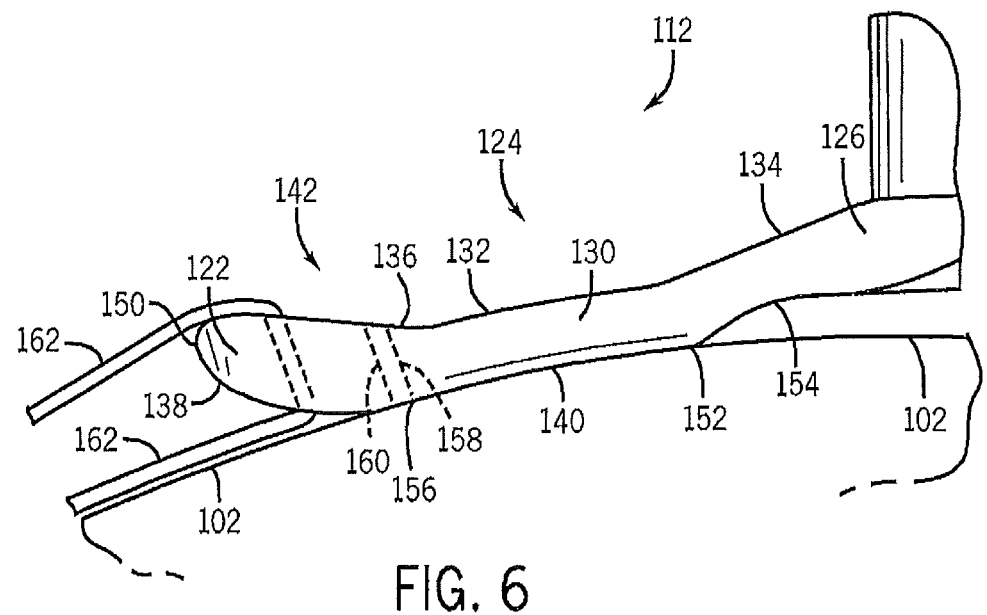
FIG. 6 is a side view of the flange section of the neck flange once secured to the patient's neck using tape and/or straps.

FIG. 6 is a side view of a flange section 124 of the neck flange 112 once secured to the patient's neck using tape and/or straps, in accordance with aspects of the present invention. As illustrated, once a strap 162 has been attached through the tie hole 142, the filleted nature of the filleted end 122 enables the strap 162 to separate from the patient's neck, thereby reducing contact with the patient 102 and reducing friction and irritation caused by movement of the strap 162. In addition, as illustrated, the amount of hard edges contacting the patient's 102 neck is minimized. As such, the friction and irritation caused by hard edges or the strap 162 may also be reduced.

In certain embodiments, the tracheostomy tube 100 described herein may be made from suitable materials such as polyurethane, polyvinyl chloride (PVC), polyethylene teraphthalate (PETP), low-density polyethylene (LDPE), polypropylene, silicone, neoprene, polytetrafluoroethylene (PTFE), or polyisoprene.

It should be understood that the fillet may have various shapes and profiles, including generally planar, curved, three-dimensionally angled or curved, and so forth. That is, from a point where the fillet joins the bottom surface of the flange, the lower surface of the flange rises with respect to the bottom surface. This rise may follow a generally linear path (similar to a chamfer), or a curved path. To minimize irritation, the transitions will typically be smooth and rounded (e.g., between the bottom surface and the onset of the fillet). However, regardless of the particular shape, the raised lower surface will aid in elevating the tip of the flange above the skin of the neck when the tube is in use and secured to the patient's neck via a tie, tape, or other structure (typically installed through the tie holes on the opposing flanges).

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheostomy tube, comprising:
   a cannula configured to be inserted into a trachea of a patient;
   a connector coupled to a proximal end of the cannula; and
   a tracheostomy tube flange coupled to the connector at a first end and extending away from the connector and terminating at a second end, wherein the first end and the second end angle downward towards a center portion of the tracheostomy tube flange such that the first end and the second end are raised relative to a top surface of the center portion and wherein the second end comprises a filleted end that gradually thickens away from the center portion.

2. The tracheostomy tube of claim 1, wherein the second end comprises a tapered top surface.

3. The tracheostomy tube of claim 2, wherein the tapered top surface comprises a taper angle of 25-35 degrees.

4. The tracheostomy tube of claim 1, comprising a tie hole oriented entirely within the filleted end.

5. The tracheostomy tube of claim 1, wherein a portion of a bottom surface of the second end is raised relative to a bottom surface of the center portion.

6. The tracheostomy tube of claim 1, wherein a portion of a bottom surface of the first end is raised relative to a bottom surface of the center portion.

7. The tracheostomy tube of claim 1, wherein the tracheostomy tube flange comprises two side surfaces from the top surface to a bottom surface, and the filleted end comprises curved edges from the side surfaces to a tip of the tracheostomy tube flange.

8. The tracheostomy tube of claim 1, wherein the connector has a sloped surface at a distal end, and wherein the first end is adjacent to the sloped surface.

9. The tracheostomy tube of claim 1, wherein a total length of the tracheostomy flange between the connector and the second end is between approximately 1.5 inches and 2.5 inches.

10. The tracheostomy tube of claim 9, wherein a length of the first end between the connector and the center portion is between approximately 20% and 30% of the total length of the tracheostomy flange.

11. The tracheostomy tube of claim 9, wherein a length of the center portion is between approximately 40% and 60% of the total length of the tracheostomy flange.

12. The tracheostomy tube of claim 9, wherein a length of the second end between the center portion and the filleted end of the tracheostomy flange is between approximately 20% and 30% of the total length of the tracheostomy flange.

13. The tracheostomy tube of claim 1, wherein the first end comprises a tapered surface.

14. The tracheostomy tube of claim 13, wherein the tapered surface comprises a taper angle of between approximately 25 degrees and 35 degrees.

15. The tracheostomy tube of claim 1, wherein the center portion comprises a substantially flat surface.

16. The tracheostomy tube of claim 1, wherein the tracheostomy flange is coupled to a distal end of the connector.

17. The tracheostomy tube of claim 1, wherein the filleted end comprises a curved edge extending to a side surface of the center portion.

18. A connector for a tracheostomy tube, comprising:
   a body comprising a proximal end, a distal end, and a central bore, wherein the distal end is configured to be coupled to a tracheostomy tube;
   a flange coupled to the body at a first end and extending away from the body and terminating at a second end, wherein the first end and the second end angle downward towards a center portion of the flange such that the first end and the second end are raised relative to a top surface of the center portion and wherein the second end comprises a filleted end that gradually thickens away from the center portion.

19. The connector of claim 18, wherein the second end comprises a tapered top surface comprising a taper angle of 25-35 degrees.

20. The connector of claim 18, wherein a portion of a first bottom surface of the second end and a second bottom surface of the first end are raised relative to a bottom surface of the center portion.

* * * * *